(12) United States Patent
Yokoyama

(10) Patent No.: US 9,482,632 B2
(45) Date of Patent: Nov. 1, 2016

(54) ABNORMALITY DETECTION DEVICE

(71) Applicant: NEC Corporation, Tokyo (JP)

(72) Inventor: Jun Yokoyama, Tokyo (JP)

(73) Assignee: NEC Corporation, Tokyo (JP)

( * ) Notice: Subject to any disclaimer, the term of this patent is extended or adjusted under 35 U.S.C. 154(b) by 419 days.

(21) Appl. No.: 14/018,152

(22) Filed: Sep. 4, 2013

(65) Prior Publication Data

US 2014/0064321 A1 Mar. 6, 2014

(30) Foreign Application Priority Data

Sep. 5, 2012 (JP) .................................. 2012-194793

(51) Int. Cl.
*G01N 25/72* (2006.01)
*H05K 7/20* (2006.01)

(52) U.S. Cl.
CPC .......... *G01N 25/72* (2013.01); *H05K 7/20836* (2013.01)

(58) Field of Classification Search
CPC .... G01N 25/72; H05K 7/20836; G01K 7/42; G01K 7/425
USPC .............................................................. 374/4
See application file for complete search history.

(56) References Cited

U.S. PATENT DOCUMENTS

| | | | | |
|---|---|---|---|---|
| 2002/0135496 A1* | 9/2002 | Takehara | ............... | G01K 1/026 340/870.17 |
| 2006/0231639 A1* | 10/2006 | Harper | ..................... | G01K 7/42 236/94 |
| 2007/0215341 A1* | 9/2007 | Urita | ...................... | G06F 1/206 165/287 |
| 2008/0040067 A1* | 2/2008 | Bashor | .................... | G06F 11/24 702/132 |
| 2009/0323277 A1* | 12/2009 | Hosokawa | .............. | G06F 1/203 361/679.54 |
| 2010/0030395 A1* | 2/2010 | Shimotono | ............. | G06F 1/206 700/300 |
| 2011/0057803 A1* | 3/2011 | Yamaoka | ........... | H05K 7/20836 340/584 |
| 2011/0295443 A1* | 12/2011 | Shah | .................. | G05D 23/1932 700/300 |

FOREIGN PATENT DOCUMENTS

| | | |
|---|---|---|
| JP | 2006-127283 | 5/2006 |
| JP | 2007-226617 A | 9/2007 |
| JP | 2007-249719 A | 9/2007 |
| JP | 2008-034715 A | 2/2008 |
| JP | 2009-205240 A | 9/2009 |
| JP | 2010-009539 A | 1/2010 |
| JP | 2011-059739 A | 3/2011 |

OTHER PUBLICATIONS

Japanese Office Action issued by the Japan Patent Office for Application No. 2012-194793 dated Aug. 2, 2016 (7 pages).

* cited by examiner

*Primary Examiner* — Lisa Caputa
*Assistant Examiner* — Philip Cotey
(74) *Attorney, Agent, or Firm* — Wilmer Cutler Pickering Hale and Dorr LLP

(57) ABSTRACT

An estimating unit 51 estimates the upper limit of possible temperatures in a predetermined position of ICT equipment when the quantity of intake air into the ICT equipment is appropriate, based on the result of detection by an operational status detecting unit that detects the operational status of the ICT equipment and the result of detection by an intake-air temperature sensor 62 that detects the temperature of intake air of the ICT equipment. A determining unit 52 determines that an abnormality is occurring when the result of detection by a temperature sensor 63 that detects the temperature in the predetermined position is beyond the upper limit estimated by the estimating unit.

9 Claims, 5 Drawing Sheets

FIG. 3

165 FAN-ROTATION-NUMBER AND
TEMPERATURE-RANGE STORING PART

| INTAKE-AIR TEMPERATURE | CPU LOAD | FAN ROTATION NUMBER | EXHAUST-AIR TEMPERATURE RANGE | CPU TEMPERATURE RANGE |
|---|---|---|---|---|
| $Ta1 \leq Ta < Ta2$ | $L1 \leq L < L2$ | R1 | $Tb1 \leq Tb < Tb2$ | $Tc1 \leq Tc < Tc2$ |
| $Ta1 \leq Ta < Ta2$ | $L2 \leq L < L3$ | R2 | $Tb2 \leq Tb < Tb3$ | $Tc2 \leq Tc < Tc3$ |
| ⋮ | ⋮ | ⋮ | ⋮ | ⋮ |
| $Ta1 \leq Ta < Ta2$ | $L10 \leq L < L11$ | R10 | $Tb10 \leq Tb < Tb11$ | $Tc10 \leq Tc < Tc11$ |
| $Ta2 \leq Ta < Ta3$ | $L1 \leq L < L2$ | R1' | $Tb1' \leq Tb < Tb2'$ | $Tc1' \leq Tc < Tc2'$ |
| $Ta2 \leq Ta < Ta3$ | $L2 \leq L < L3$ | R2' | $Tb2' \leq Tb < Tb3'$ | $Tc2' \leq Tc < Tc3'$ |
| ⋮ | ⋮ | ⋮ | ⋮ | ⋮ |
| $Ta2 \leq Ta < Ta3$ | $L10 \leq L < L11$ | R10' | $Tb10' \leq Tb < Tb11'$ | $Tc10' \leq Tc < Tc11'$ |
| ⋮ | ⋮ | ⋮ | ⋮ | ⋮ |

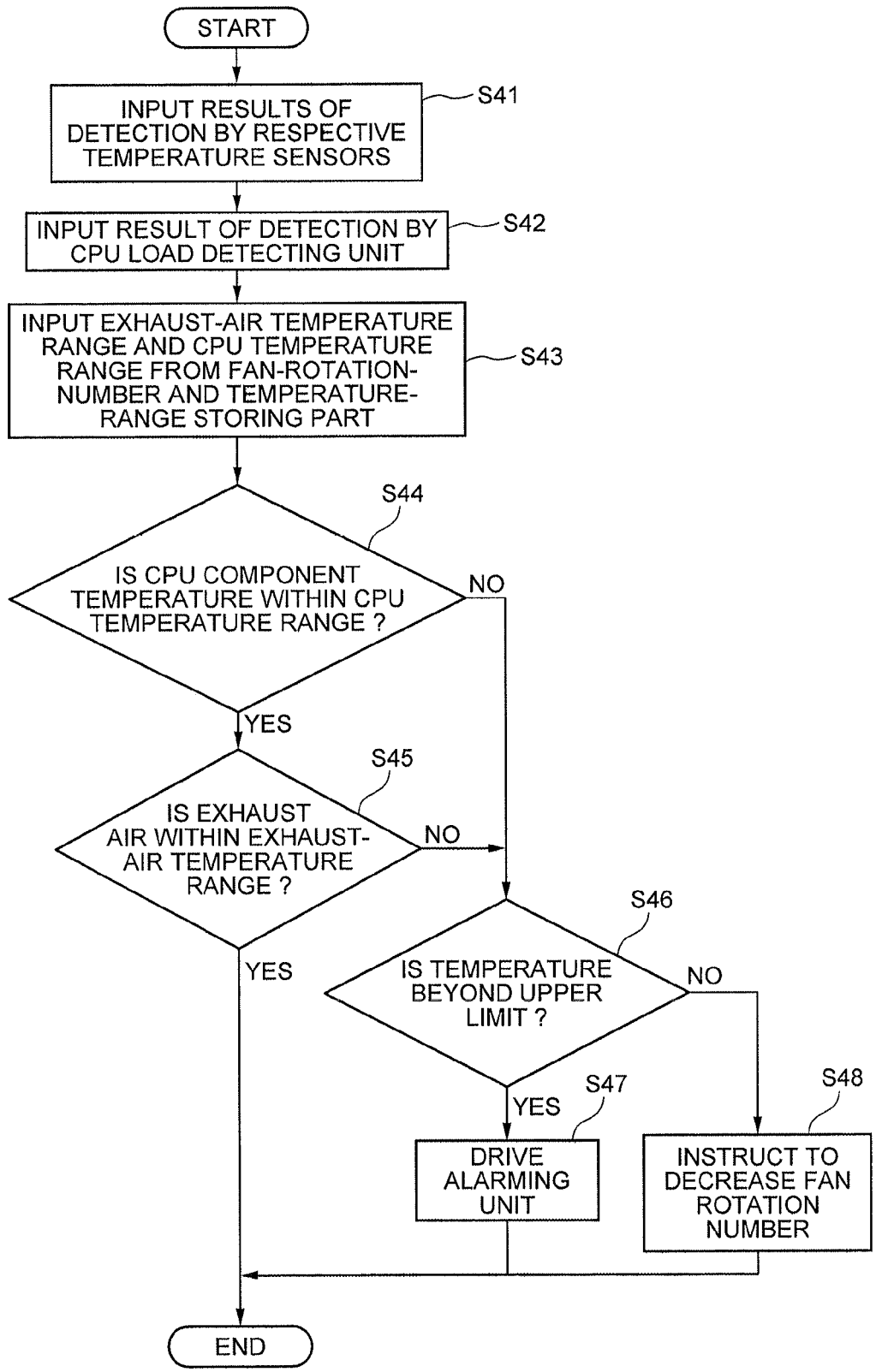

ABNORMALITY DETECTION DEVICE

INCORPORATION BY REFERENCE

This application is based upon and claims the benefit of priority from Japanese patent application No. 2012-194793, filed on Sep. 5, 2012, the disclosure of which is incorporated herein in its entirety by reference.

TECHNICAL FIELD

The present invention relates to an abnormality detection device that detects an abnormality of a cooling function of ICT (Information and Communication Technology) equipment such as a server, and also relates to ICT equipment, an abnormality detection method, and a program.

BACKGROUND ART

ICT equipment such as a server may have a cooling fan within a case thereof so as to prevent the internal temperature of the case from excessively rising due to heat generation by an electronic component such as a CPU. Rotation of the cooling fan allows air to be taken in through an inlet opening formed on the case, and the inside of the case is thereby cooled down. A filter is attached to the inlet opening, so that dust does not enter the case. Even if the cooling fan is attached, however, when the filter is clogged or the cooling fan is down, the quantity of intake air decreases, and the inside of the case cannot be cooled down. In a case where the inside of the case cannot be cooled down, the ICT equipment cannot operate normally.

As a technique for solving such a problem, the following technique is known (e.g., see Patent Document 1). In the technique described in Patent Document 1, firstly, the temperature of intake air and the temperature of a CPU are detected, and an allowable temperature defined for the intake-air temperature is obtained. Then, the CPU temperature is compared with the allowable temperature and, when the CPU temperature is beyond the allowable temperature, it is examined whether the number of rotations of the cooling fan is a set number of rotations. It is notified to the user that the filter is clogged when the number of rotations of the cooling fan is the set number of rotations, whereas it is notified to the user that the cooling fan is down when the number of rotations of the cooling fan is not the set number of rotations.

[Patent Document 1] Japanese Unexamined Patent Application Publication No. JP-A 2006-127283

In a case where the operational status of the ICT equipment is constant, it is possible to accurately detect an abnormality such as clogging of the filter by the technique described in Patent Document 1. However, in the technique described in Patent Document 1, the CPU temperature is compared with the allowable temperature defined for the intake-air temperature, and it is thereby determined whether an abnormality such as clogging of the filter is occurring. Therefore, in a case where the operational status of the ICT equipment is not constant, it may be impossible to detect an abnormality such as clogging or, by contrast, it may be determined that an abnormality such as clogging is occurring in spite of no abnormality. For example, in the latest ICT equipment, the amount of heat generated by the CPU substantially triples depending on the operational status and this fact is not considered in the technique described in Patent Document 1, so that it is impossible to accurately detect an abnormality such as clogging of the filter.

SUMMARY

Accordingly, an object of the present invention is to provide an abnormality detection device that solves a problem such that it is impossible to accurately detect an abnormality of a cooling function, such as clogging of a filter, in a case where the operational status of ICT equipment is not constant.

An abnormality detection device according to the present invention, comprising:

an estimating unit configured to estimate an upper limit of possible temperatures in a predetermined position of ICT equipment when a quantity of intake air into the ICT equipment is appropriate, based on a result of detection by an operational status detecting unit that detects an operational status of the ICT equipment and a result of detection by an intake-air temperature sensor that detects a temperature of intake air of the ICT equipment; and a determining unit configured to determine that an abnormality is occurring when a result of detection by a temperature sensor that detects a temperature in the predetermined position is beyond an upper limit estimated by the estimating unit.

ICT equipment according to the present invention, comprising:

an operational status detecting unit configured to detect an operational status of the ICT equipment;

an intake-air temperature sensor configured to detect a temperature of intake air of the ICT equipment;

a temperature sensor configured to detect a temperature in a predetermined position of the ICT equipment;

an estimating unit configured to estimate an upper value of possible temperatures in a predetermined position of the ICT equipment when a quantity of intake air into the ICT equipment is appropriate, based on a result of detection by the operational status detecting unit and a result of detection by the intake-air temperature sensor; and a determining unit configured to determine that an abnormality is occurring when a result of detection by the temperature sensor is beyond an upper limit estimated by the estimating unit.

An abnormality detection method according to the present invention, comprising:

by an estimating unit, estimating an upper limit of possible temperatures in a predetermined position of ICT equipment when a quantity of intake air into the ICT equipment is appropriate, based on a result of detection by an operational status detecting unit that detects an operational status of the ICT equipment and a result of detection by an intake-air temperature sensor that detects a temperature of intake air of the ICT equipment; and by a determining unit, determining that an abnormality is occurring when a result of detection by a temperature sensor that detects a temperature in the predetermined position is beyond an upper limit estimated by the estimating unit.

A computer program according to the present invention, comprising instructions for causing a computer to function as:

an estimating unit configured to estimate an upper limit of possible temperatures in a predetermined position of ICT equipment when a quantity of intake air into the ICT equipment is appropriate, based on a result of detection by an operational status detecting unit that detects an operational status of the ICT equipment and a result of detection by an intake-air temperature sensor that detects a temperature of intake air of the ICT equipment; and a determining unit configured to determine that an abnormality is occurring when a result of detection by a temperature sensor that detects a temperature in the predetermined position is beyond an upper limit estimated by the estimating unit.

According to the present invention, even when the operational status of ICT equipment is variable, it is possible to securely detect an abnormality of a cooling function, such as clogging of a filter.

BRIEF DESCRIPTION OF DRAWINGS

FIG. 3 is a view showing an example of the content of a fan-rotation-number and temperature-range storing part disclosed in FIG. 2;

FIG. 4 is a flowchart showing an example of processing by the management part disclosed in FIG. 1.

EXEMPLARY EMBODIMENT

Next, exemplary embodiments of the present invention will be described in detail with reference to the drawings.

First Exemplary Embodiment of the Present Invention

Figure 1:
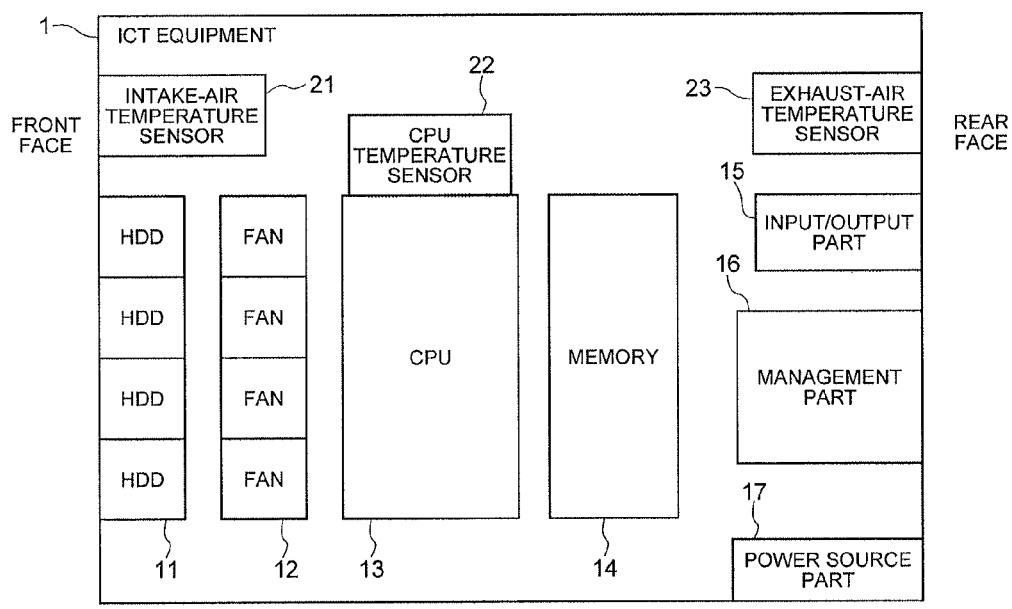
FIG. 1 is a block diagram showing an example of the configuration of ICT equipment 1 according to a first exemplary embodiment of the present invention.

Referring to FIG. 1, ICT equipment 1 according to a first exemplary embodiment of the present invention has, on the front side in a case thereof, a plurality of hard disk drives (HDDs) 11 and an intake-air temperature sensor 21 detecting the temperature of intake air, and in the rear of them, has a plurality of cooling fans (FANs) 12. In the rear of the cooling fans 12, a CPU 13 generating much heat and a CPU temperature sensor 22 detecting the component temperature of the CPU 13 are arranged. Moreover, in the rear of them, a memory 14, an input/output part 15, a management part 16 that is realized by a chip set, a BMC (Base Management Controller) and the like and functions as a control device, a power source part 17, and an exhaust-air temperature sensor 23 detecting the temperature of exhaust air are arranged.

When the cooling fans 12 rotate, air is taken in through an inlet opening (not shown) formed on the front face of the case. The intake air flows toward the rear face of the case and is exhausted through an outlet opening (not shown) formed on the rear face of the case. A filter for excluding dust is attached to the inlet opening.

Figure 2:
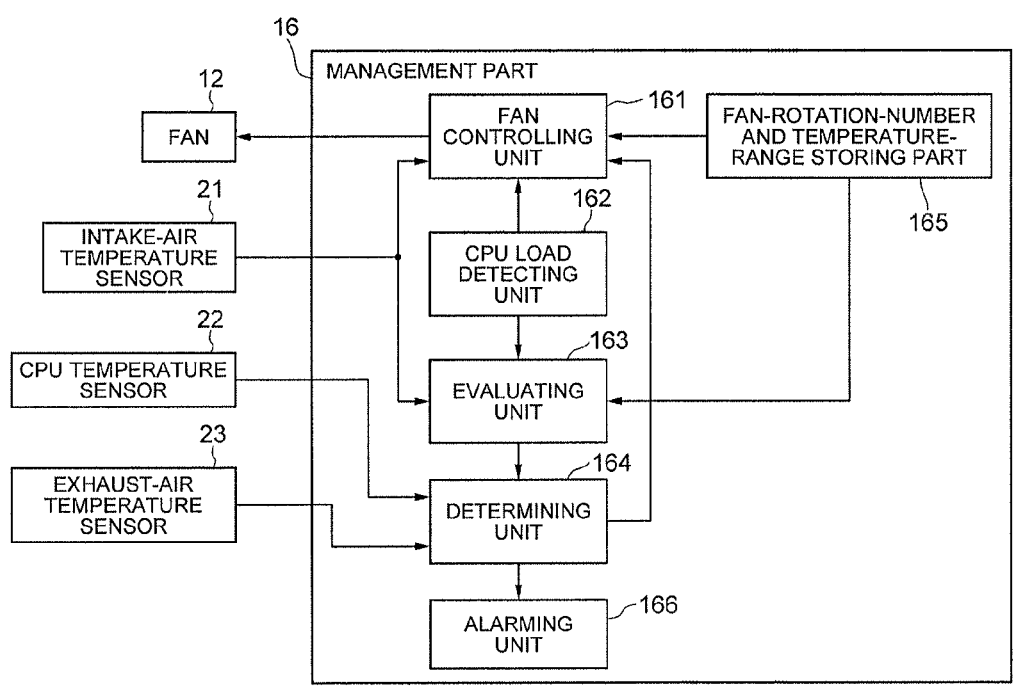
FIG. 2 is a block diagram showing an example of the configuration of a management part disclosed in FIG. 1.

Referring to FIG. 2, the management part 16 includes a fan controlling unit 161, a CPU load detecting unit 162, an estimating unit 163, a determining unit 164, a fan-rotation-number and temperature-range storing part 165, and an alarming unit 166 such as a buzzer or an LED.

The fan-rotation-number and temperature-range storing unit 165 stores the number of rotations of the fans, the range of intake-air temperatures, and the range of CPU temperatures, in association with a combination of the temperature of intake air and a load on the CPU. FIG. 3 is a view showing an example of the stored content in the fan-rotation-number and temperature-range storing part 165. In this exemplary embodiment, in a case where an intake-air temperature Ta is equal, the upper limits and the lower limits of the exhaust-air temperature range and the CPU temperature range are lower as a CPU load L is smaller.

For example, the second row in FIG. 3 shows that the number of rotations of the cooling fans 12 is R2 in a case where the intake-air temperature Ta is $Ta1 \leq Ta < Ta2$ and the CPU load L is $L2 \leq L < L3$. Also, the second row shows that, in a case where the intake-air temperature Ta is $Ta1 \leq Ta < Ta2$ and the CPU load L is $L2 \leq L < L3$, the exhaust-air temperature range estimated as a possible range of exhaust-air temperatures Tb when the intake quantity of air into the case (an air intake quantity per unit time) is $Tb2 \leq Tb < Tb3$ and the CPU temperature range estimated as a possible range of component temperatures Tc of the CPU 13 is $Tc2 \leq Tc < Tc3$.

The exhaust-air temperature range and the CPU temperature range are determined based on the values of exhaust-air temperatures and CPU temperatures actually measured when the ICT equipment 1 is normally operating (when an abnormality like clogging of the filter is not occurring). In this exemplary embodiment, the fan-rotation-number and temperature-range storing part 165 storing the fan rotation number, the exhaust-air temperature range and the CPU temperature range in association with the combination of the intake-air temperature and the CPU load is employed, but it is not necessarily employed. A fan-rotation-number storing part that stores the fan rotation number in association with the combination of the intake-air temperature and the CPU load, and a temperature-range storing part that stores the exhaust-air temperature range and the CPU temperature range in association with the combination of the intake-air temperature and the CPU load may be employed instead of the fan-rotation-number and temperature-range storing part 165.

The CPU load detecting unit 162 has a function of detecting the load on the CPU 13. In this exemplary embodiment, the use rate of the CPU 13 is detected as the load on the CPU 13. The CPU load detecting unit 162 is used for detecting the operational status of the ICT equipment 1. As far as being capable of detecting the operational status of the ICT equipment 1, another unit such as a power consumption detecting unit that detects the power consumption of the ICT equipment 1 may be used.

The fan controlling unit 161 has a function of: determining the number of rotations of the cooling fans 12, based on the result of detection by the intake-air temperature sensor 21, the result of detection by the CPU load detecting unit 162 and the content of the fan-rotation-number and temperature-range storing part 165; and causing the cooling fans 12 to rotate at the determined number of rotations. To be specific, the fan controlling unit 161 searches the number of rotations stored in association with a combination of the result of detection by the intake-air temperature sensor 21 and the result of detection by the CPU load detecting unit 162, from the fan-rotation-number and temperature-range storing part 165, and causes the cooling fans 12 to rotate at the searched number of rotations.

The estimating unit 163 has a function of calculating an exhaust-air temperature range estimated as a possible range of exhaust-air temperatures when the intake quantity of air into the case per unit time is appropriate, based on the result of detection by the intake-air temperature sensor 21, the result of detection by the CPU load detecting unit 162, and the content of the fan-rotation-number and temperature-range storing part 165. Moreover, the estimating unit 163 has a function of calculating a CPU temperature range estimated as a possible range of component temperatures of the CPU 13 when the intake quantity of air into the case per unit time is appropriate, based on the result of detection by the intake-air temperature sensor 21, the result of detection by the CPU load detecting unit 162, and the content of the fan-rotation-number and temperature-range storing part 165. To be specific, the estimating unit 163 has a function of searching an exhaust-air temperature range and a CPU temperature range stored in association with the result of detection by the intake-air temperature sensor 21 and the result of detection by the CPU load detecting unit 162, from the fan-rotation-number and temperature-range storing part 165.

The determining unit 164 has a function of determining whether an abnormality of a cooling function such as clogging of the filter is occurring, based on the CPU temperature range and the exhaust-air temperature range calculated by the estimating unit 163, the result of detection by the CPU temperature sensor 22, and the result of detection by the exhaust-air temperature sensor 23.

The management part 16 can be realized by a CPU (central processing unit), for example, by causing the CPU to read a program, which is recorded on a disk, a semiconductor memory or another recording medium, for making the CPU function as the fan controlling unit 161, the CPU load detecting unit 162, the estimating unit 163 and the determining unit 164. Then, the CPU controls the operation thereof in accordance with the program read thereby to realize the fan controlling unit 161, the CPU load detecting unit 162, the estimating unit 163 and the determining unit 164 thereon.

Operation of First Exemplary Embodiment

Next, the operation of this exemplary embodiment will be described in detail.

The management part 16 executes a process shown in a flowchart of FIG. 4 at every given time.

The estimating unit 163 inputs the results of detection by the intake-air temperature sensor 21, the CPU temperature sensor 22 and the exhaust-air temperature sensor 23 at step S41, and then inputs the result of detection by the CPU load detecting unit 162 at step S42. After that, the estimating unit 163 searches an exhaust-air temperature range and a CPU temperature range recorded in association with a combination of the result of detection by the intake-air temperature sensor 21 and the result of detection by the CPU load detecting unit 162, from the fan-rotation-number and temperature-range storing part 165, and passes the search result to the determining unit 164 (step S43).

Upon reception of the search result from the estimating unit 163, the determining unit 164 determines whether the result of detection by the CPU temperature sensor 22 is within the CPU temperature range passed from the estimating unit 163 (step S44).

In a case where the actual component temperature of the CPU 13 detected by the CPU temperature sensor 22 is within the CPU temperature range (Yes at step S44), the determining unit 164 determines whether the result of detection by the exhaust-air temperature sensor 23 is within the exhaust-air temperature range (step S45). In a case where the actual exhaust-air temperature detected by the exhaust-air temperature sensor 23 is within the exhaust-air temperature range (Yes at step S45), the determining unit 164 determines that an abnormality such as clogging of the filter is not occurring, and ends the procedure.

On the other hand, when the determining unit 164 determines that the result of detection by the CPU temperature sensor 22 is not within the CPU temperature range (the determination result is No) at step S44, the determining unit 164 examines whether the component temperature as the result of detection by the CPU temperature sensor 22 is beyond the upper limit of the CPU temperature range (step S46).

When the component temperature of the CPU 13 is beyond the upper limit of the CPU temperature range (Yes at step S46), the determining unit 164 determines that an abnormality of the cooling function such as clogging of the filter is occurring, and drives the alarming unit 166 (step S47).

On the other hand, when the component temperature of the CPU 13 is not beyond the upper limit of the CPU temperature range (No at step S46), herein, when the component temperature of the CPU 13 is below the lower limit of the CPU temperature range, the determining unit 164 proceeds to step S48. In this case, the determining unit 164 determines that the internal temperature of the ICT equipment 1 will not excessively rise even if the number of rotations of the cooling fans 12 is reduced for the purpose of reduction of the power consumption, and notifies a reduction level A of the number of rotations of the cooling fans 12 to the fan controlling unit 161 (step S48). Consequently, the fan controlling unit 161 decreases the number of rotations of the cooling fans 12 by the notified reduction level A.

The reduction level A can be a value corresponding to a difference between the lower limit of the CPU temperature range and the actual component temperature of the CPU 13 (the result of detection by the CPU temperature sensor 22). To be specific, the reduction level A is set to a larger value as the difference is larger. Moreover, the intake-air temperature and the structure of the ICT equipment 1 may be considered at the time of determination of the reduction level A. The component temperature of the CPU 13 falls below the lower limit of the CPU temperature range, for example, in a case where the cooling fans are installed outside the ICT equipment 1 after the ICT equipment 1 is installed.

Further, when the determining unit 164 determines that the exhaust-air temperature as the result of detection by the exhaust-air temperature sensor 23 is not within the exhaust-air temperature range (the determination result is No) at step S45, the determining unit 164 examines whether the result of detection by the exhaust-air temperature sensor 23 is beyond the upper limit of the exhaust-air temperature range (step S46).

When the exhaust-air temperature detected by the exhaust-air temperature sensor 23 is beyond the upper limit of the exhaust-air temperature range (Yes at step S46), the determining unit 164 determines that an abnormality such as clogging of the filter is occurring, and drives the alarming unit 166 (step S47). On the other hand, when the exhaust-air temperature is not beyond the upper limit of the exhaust-air temperature range (No at step S46), the determining unit 164 determines that the internal temperature of the ICT equipment 1 will not excessively rise even if the number of rotations of the cooling fans 12 is reduced, and notifies a reduction level A of the number of rotations of the cooling fans 12 to the fan controlling unit 161 (step S48). In this case, the reduction level A can be a value corresponding to a difference between the lower limit of the exhaust-air temperature range and the result of detection by the exhaust-air temperature sensor 23.

Effect of First Exemplary Embodiment

According to this exemplary embodiment, even when the operational status of the ICT equipment 1 is variable, it is possible to securely detect an abnormality such as clogging of the filter. This is because a temperature range estimated as a possible range of component temperatures of the CPU 13 and an exhaust-air temperature range estimated as a possible range of exhaust-air temperatures when the intake quantity of air is appropriate are calculated based on the result of detection by the intake-air temperature sensor 21 and the result of detection by the CPU load detecting unit (an operational status detecting unit) 162.

Further, according to this exemplary embodiment, it is possible to reduce the power consumption of the ICT equipment 1. This is because the number of rotations of the cooling fans 12 is reduced when the component temperature of the CPU 13 falls below the lower limit of the CPU temperature range or when the exhaust-air temperature falls below the lower limit of the exhaust-air temperature range.

Further, according to this exemplary embodiment, even if the load on the CPU 13 is small and the component temperature of the CPU 13 and the exhaust-air temperature are low, it is possible, when an abnormality such as clogging of the filter occurs, to securely detect that. This is because, as the result of detection by the CPU load detecting unit 162 indicates a lower load, the upper limits of the CPU temperature range and the exhaust-air temperature range are set to lower temperatures.

Second Exemplary Embodiment of the Present Invention

Figure 5:
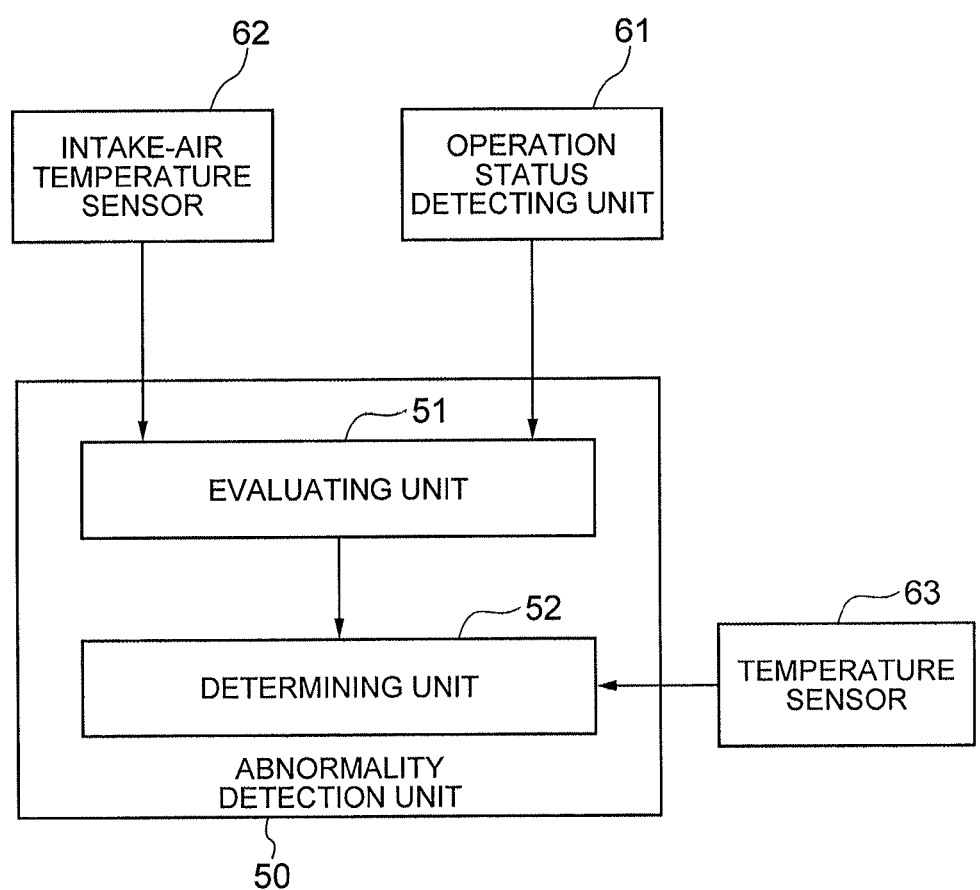
FIG. 5 is a block diagram showing an example of the configuration of an abnormality detecting unit according to a second exemplary embodiment of the present invention.

Referring to FIG. 5, an abnormality detection device 50 according to a second exemplary embodiment of the present invention includes an estimating unit 51 and a determining unit 52.

The estimating unit calculates the upper limit of temperatures estimated as a possible temperature in a predetermined position of ICT equipment when the intake quantity of air into the ICT equipment is appropriate, based on the result of detection by an operational status detecting unit 61 detecting the operational status of the ICT equipment and the result of detection by an intake-air temperature sensor 62 detecting the intake-air temperature of the ICT equipment. The determining unit 51 determines that an abnormality is occurring when the result of the detection by a temperature sensor 63 detecting the temperature in the predetermined position is beyond the upper limit calculated by the estimating unit 51.

The abnormality detection device 50 can be realized by a computer, for example, by causing the computer to read a program, which is recorded on a disk, a semiconductor memory or another recording medium, for making the computer function as the abnormality detection device 50. Then, the computer controls the operation thereof in accordance with the program read thereby to realize the estimating unit 51 and the determining unit 52 thereon.

Effect of Second Exemplary Embodiment

According to this exemplary embodiment, it is possible to securely detect an abnormality such as clogging of the filter even when the operational status of the ICT equipment is variable. This is because the upper limit of temperatures estimated as a possible temperature in a predetermined position of the ICT equipment when the intake quantity of air into the ICT equipment is appropriate is calculated based on the result of detection by the operational status detecting unit 61 detecting the operational status of the ICT equipment and the result of detection by the intake-air temperature sensor 62 detecting the intake-air temperature of the ICT equipment.

The present invention can be applied to ICT equipment such as a server.

The invention claimed is:

1. An abnormality detection device for detecting an abnormality in Information and Communication Technology (ICT) equipment having a cooling fan, the abnormality detection device comprising:
   a hardware processor comprising:
      an estimating unit configured to estimate an upper limit of possible temperatures in a predetermined position of ICT equipment when a quantity of intake air into the ICT equipment is appropriate, based on a result of detection by an operational status detecting unit that detects an operational status of the ICT equipment and a result of detection by an intake-air temperature sensor that detects an intake air temperature of intake air of the ICT equipment, wherein the operational status of the ICT equipment and the intake air temperature of the ICT equipment determines a rotation speed of the cooling fan; and
      a determining unit configured to determine that an abnormality is occurring when a result of detection by a temperature sensor that detects a detected equipment temperature in the predetermined position is beyond the upper limit estimated by the estimating unit.

2. The abnormality detection device according to claim 1, wherein the estimating unit is configured to, in a case where a result of detection by the intake-air temperature sensor is equal, estimate a lower temperature value as the upper limit, as the operational status detected by the operational status detecting unit indicates a lower utilization rate.

3. The abnormality detection device according to claim 1, comprising a temperature range storing part in which the upper limit of the possible temperatures in the predetermined position is recorded in association with each combination of a first utilization rate and a temperature of intake air, and the upper limit of the possible temperatures in the predetermined position is recorded in association with each combination of a second utilization rate that is larger than the first utilization rate and a temperature of intake air,
   wherein the estimating unit is configured to search an upper limit that is recorded in association with a temperature of intake air detected by the intake-air temperature sensor and a utilization rate detected by the operational status detecting unit, from the temperature range storing unit.

4. The abnormality detection device according to claim 1, wherein:
   the estimating unit is configured to estimate a lower limit of the possible temperatures in the predetermined position when a quantity of intake air into the ICT equipment is appropriate, based on a result of detection by the operational status detecting unit and a result of detection by the intake-air temperature sensor; and
   the determining unit is configured to instruct a fan controlling unit that controls a number of rotations of cooling fans to reduce a number of rotations of the cooling fans when a result of detection by the temperature sensor is below a lower limit estimated by the estimating means.

5. The abnormality detection device according to claim 1, wherein the operational status detecting unit is configured to detect a load on a CPU mounted in the ICT equipment as an operational status of the ICT equipment.

6. The abnormality detection device according to claim 1, wherein the operational status detecting unit is configured to detect power consumption of the ICT equipment as an operational status of the ICT equipment.

7. The abnormality detection device according to claim 1, wherein the temperature sensor is configured to detect a temperature of exhaust air.

8. An Information and Communication Technology (ICT) equipment including a cooling fan, comprising:
   an operational status detecting unit configured to detect an operational status of the ICT equipment;
   an intake-air temperature sensor configured to detect an intake air temperature of intake air of the ICT equipment;
   an equipment temperature sensor configured to detect an equipment temperature in a predetermined position of the ICT equipment;
   a hardware processor including:
      an operational status detecting unit configured to detect an operational status of the ICT equipment;
      an estimating unit configured to estimate an upper value limit of possible temperatures in a predetermined position of the ICT equipment when a quantity of intake air into the ICT equipment is appropriate, based on a result of detection by the operational status detecting unit and a result of detection by the intake-air temperature sensor, an operational status of the ICT equipment, and an intake air temperature, wherein the operational status of the ICT equipment and the intake air temperature of the ICT equipment determines a rotation speed of the cooling fan; and
      a determining unit configured to determine that an abnormality is occurring when a result of detection by the detected equipment temperature sensor is beyond the upper limit estimated by the estimating unit.

9. An abnormality detection method of Information and Communication Technology (ICT) equipment including a cooling fan, the method comprising:
   detecting an operational status and an intake air temperature of the ICT equipment;
   by an estimating unit, estimating an upper limit of possible temperatures in a predetermined position of the ICT equipment when a quantity of intake air into the ICT equipment is appropriate, based on the detected operational status and the air intake temperature, a result of detection by an operational status detecting unit that detects an operational status of the ICT equipment and a result of detection by an intake-air temperature sensor that detects a temperature of intake air of the ICT equipment;
   determining a rotation speed of the cooling fan based on the detected operational status and the air intake temperature; and
   by a determining unit, determining that an abnormality is occurring when a result of detection by a detected equipment temperature sensor that detects a temperature in the predetermined position is beyond the upper limit estimated by the estimating unit.

* * * * *